United States Patent [19]

Rautenberg et al.

[11] Patent Number: 5,439,799
[45] Date of Patent: Aug. 8, 1995

[54] AGENT AND PROCESS FOR TREATING BODY FLUIDS IN THE DETERMINATION OF NEOPTERIN

[75] Inventors: Wilfried Rautenberg, Reinheim; Arnulf Heubner, Mainz, both of Germany

[73] Assignee: Merck Patent Gesellschaft mit Beschrankter Haftung, Darmstadt, Germany

[21] Appl. No.: 57,796

[22] Filed: May 7, 1993

[30] Foreign Application Priority Data

May 9, 1992 [DE] Germany .................. 42 15 275.5

[51] Int. Cl.⁶ .................................. G01N 33/545
[52] U.S. Cl. .................................. 435/7.93; 435/962; 436/531; 436/815; 436/825; 436/826
[58] Field of Search .................. 435/7.93, 7.5, 962; 436/531, 815, 825, 826

[56] References Cited

U.S. PATENT DOCUMENTS

| | | | |
|---|---|---|---|
| 4,371,514 | 2/1983 | Nagatsu et al. | 436/542 |
| 4,490,465 | 12/1984 | Limbach et al. | 435/14 |
| 4,668,620 | 5/1987 | Armenta et al. | 436/825 |
| 4,978,632 | 12/1990 | Mach et al. | 436/825 |

FOREIGN PATENT DOCUMENTS

| | | | |
|---|---|---|---|
| 12444 | 6/1980 | European Pat. Off. | |
| 68344 | 1/1983 | European Pat. Off. | 435/962 |

OTHER PUBLICATIONS

M. Barak et al., Clin. Chem., 35/7, 1467–1471 (1989). Neopterin Meausred in Serum and Tissue Culture Supernates by a Competitive ELISA.

*Primary Examiner*—Mary E. Ceperley
*Attorney, Agent, or Firm*—Millen, White, Zelano & Branigan

[57] ABSTRACT

The invention relates to an agent and process for treating body fluids in the immunological determination of neopterin using a specific antibody against neopterin and a detection system. The agent is characterized in that it contains an oxidizing agent.

17 Claims, No Drawings

AGENT AND PROCESS FOR TREATING BODY FLUIDS IN THE DETERMINATION OF NEOPTERIN

BACKGROUND OF THE INVENTION

The invention relates to an agent and process for treating body fluids in the immunological determination of neopterin using a specific antibody against neopterin and a detection system.

Since the discovery of neopterin in the urine of patients with malignant or viral diseases in 1979, neopterin has become established as a parameter for ascertaining the cellular immune status in a multitude of patients with many different kinds of diseases.

Neopterin belongs to the pteridine group of compounds, which are heterocyclic molecules with a wide distribution in the plant and animal kingdoms. While some biological functions of pteridines are well documented, the biological role of neopterin is thus far largely unknown.

Neopterin is produced by monocytes/macrophages following induction by interferon gamma; interferon gamma is in turn directly coupled to the activation of cell-mediated immunity, and is formed by activated T-lymphocytes, when these are stimulated.

Cellular immunity plays a decisive role in a series of diseases, such as viral infections, intracellular parasites, septicaemia, graft rejections, autoimmune disorders and neoplasias. Raised concentrations of neopterin in body fluids directly reflect the degree of activation of the cellular immune system. Thus, determination of the concentration of neopterin in body fluids is very suitable indeed for monitoring the cellular immune status.

The determination of neopterin in body fluids for the purpose of establishing the cellular immune status in the case of malignant tumours and/or viral diseases is described, for example, in EP 12 444. Methods which have hitherto been customary for determining neopterin in body fluids, preferably in serum and urine, are high pressure liquid chromatography (HPLC), (J. Chromatogr. 277, 61 (1982)) and radioimmunoassay (Chem. Biol. Pteridines, 815 ff. W. de Gruyter, Berlin-New York (1983)). Both methods have some disadvantages, however. Neopterin can only be determined by HPLC after a relatively elaborate processing procedure. Each analysis then lasts for about a further 10 to 15 minutes, so that the measurement of a relatively large number of samples, even with automation, is associated with much expenditure of time and effort. Radioimmunoassays may only be carried out in specially approved laboratories, and specific guidelines must be followed for the safe disposal of radioactively contaminated working solutions and wastes.

In a competitive immunoassay for determining neopterin, on which the invention is based, the inner surfaces of plastic vessels, wells of a microtiter plate, polystyrene latex, glass spheres, or magnetic particles are coated, as the solid phase, with a neopterin-specific antibody. For example, the neopterin-containing samples to be analyzed and a conjugate consisting of neopterin and a marker enzyme are pipetted into the wells of a microtiter plate. The neopterin in the sample and the conjugate compete for the limited binding sites on the solid phase. High concentrations of neopterin in the sample then lead to low binding of conjugate on the solid phase. This in turn leads, after a washing step to remove all unbound substances, to low color development in a subsequent substrate reaction which is specific for the marker enzyme employed.

Quantification of the neopterin concentration in the samples is effected using a calibration curve which is plotted with standards of precisely defined neopterin concentrations. The average concentration of neopterin in the serum of healthy persons is about 5 nmol/l; values above 10 to 15 nmol/l are considered to be pathological. Because of the high sensitivity, of at least 1 nmol of neopterin/l, of the immunoassay which is required, the serum sample must be combined directly with the reaction partners, i.e. the serum must be employed in undiluted form in the assay. When this was done, however, it emerged that the neopterin determination in fresh sera, which are as a rule employed as samples, always gave measured values which were too high. For example, at a concentration of 5 nmol/l, the measured values were falsely more than 100% too high.

Elimination of interference from serum and/or other body fluids components can, as a rule, be achieved by using high dilutions of the serum, which however, is not possible because of the sensitivity required in this case. Furthermore, any possible denaturation of the sample by heat or the addition of denaturing agents is unsuitable for the neopterin determination. It turned out, however, that the interference declined during storage of the sera, and that the neopterin content can be measured correctly in older sera, as was ascertained from the very good correlations with other methods of determining neopterin. However, since the neopterin determination must as a rule be carried out in fresh sera, the falsely elevated values occurring under these circumstances are most disadvantageous for diagnostics.

SUMMARY OF THE INVENTION

An object of the invention is to make available an agent and a process for treating body fluids in the immunological determination of neopterin, which makes possible the precise determination of neopterin in fresh body fluids as well.

The invention relates to an agent for treating body fluids in the immunological determination of neopterin using a specific antibody against neopterin and a detection system, which is characterized in that it contains an oxidizing agent.

The invention additionally relates to a process for treating body fluids in the immunological determination of neopterin using a specific antibody against neopterin and a detection system, which is characterized in that the incubation of all the reaction partners is carried out in the presence of an oxidizing agent.

Surprisingly, it was found that, with the agent and process according to the invention, neopterin can be determined correctly using an immunoassay in fresh sera as well. The reagent according to the invention does not impair the immunological activity of antibodies and the enzymatic activity of marker enzymes, and is stable for at least 1 year at the storage temperatures of 2°-8° C. which are customary for clinical reagents.

Suitable oxidizing agents are, e.g., potassign or sodium hexacyanoferrate(III), iron(III) salt/chelating agent, persulfate, perborate and nitroprusside, preferably potassium hexacyanoferrate(III) at a concentration of 0.05 to 100 mmol/l, preferably 0.5 to 50 mmol/l. Similar results are also obtained with the other oxidizing agents, and/or combinations of oxidizing agents, for example with the combination iron (III) salt/chelating agent, preferably iron (III) nitrate/EDTA, in a concentration range of about 0.25 to 25 mmol/l.

The oxidizing agent according to the invention is employed in an aqueous solution which is buffered, at high ionic strength, e.g. at a pH in the range of 5 to 10 preferably 7 to 8. The buffer substances which may be used are all those buffers or buffer combinations known in clinical chemistry, e.g., which can maintain a pH range of 5 to 10, preferably 7 to 8, and which do not interfere with the test components. For example, phosphate buffer, TRIS buffer, citrate buffer and HEPES buffer are suitable, preferably phosphate buffer. The buffer concentration should be in the range of 50 to 300 mmol/l, preferably 150 to 250 mmol/l. The oxidizing agent according to the invention is optimally active within the temperature range of about 15°–40° C. which is customary in clinical chemistry.

The preparation of the specific antibody against neopterin and the binding of antibodies to a solid phase are known from the literature, e.g., Clin. Chem. 35, 1467–1471 (1989). A specific antibody of any source or isotype may be employed in the immunoassay, as long as it possesses the desired specificity for neopterin (i.e., it detects neopterin under the particular immunoassay conditions which have been chosen). For example, the specific antibody may be a monoclonal, e.g., from a mouse, or a polyctonal, e.g., prepared in a rabbit, goat, or sheep, or a chimeric antibody. The labelling of antibodies, antigens and haptens with marker enzymes is likewise a well-known method. In the test according to the invention, peroxidase and alkaline phosphatase are preferably bound to the neopterin as marker enzymes; however other marker enzymes may also be used.

The detection system is a system for detecting the marker enzyme which contains, e.g., the typical substrate solution for the marker enzyme in question, consisting of substrate, buffer, detergents, chromogen etc., as are known from clinical diagnostics, e.g., Clin. Chem. 35, 1467–1471, (1989).

An immunoassay for determining neopterin in serum is carried out as follows: the reagent solution according to the invention, standards, controls and samples are pipetted into the empty wells of a microtiter plate, whose inner surface is coated with a neopterin-specific antibody. After an incubation period, the buffered neopterin-enzyme conjugate solution is added, and the incubation is continued. After a washing step, a substrate solution which is typical for the marker enzyme is pipetted into the wells. Subsequently, the substrate reaction is stopped with a stopping reagent and the extinction of the dye which has been formed is measured at the absorption maximum. The concentration of the samples is ascertained from the plotted calibration curve. The concentration of neopterin in the sample is inversely proportional to the measured signal.

A kit comprising components necessary for the process of treating body fluids in the immunological detection of neopterin, e.g., an immunoassay, is another aspect of the invention. The kit may comprise one or more of an antibody specific for neopterin, a neopterin conjugated to a detectable label, e.g., an enzyme, biotin or avidin, a fluorescent marker, an oxidizing agent which reduces the amount of interference by body fluids in the process, buffer, enzyme substrate, microtiter wells, detergent, or any other components necessary for carrying out the process.

The entire disclosure of all applications, patents and publications, cited above and below, and of corresponding German application No. P 42 15 275.5, filed May 9, 1992 is hereby incorporated by reference.

In the foregoing and in the following examples, all temperatures are set forth uncorrected in degrees Celsius; and, unless otherwise indicated, all parts and percentages are be weight.

EXAMPLES

Example 1

Determination of neopterin using a conjugate consisting of neopterin and horseradish peroxidase

| Reagent solution: | Concentration in the reagent |
|---|---|
| Phosphate buffer, pH 7.2 | 250 mmol/l |
| Potassium hexacyanoferrate (III) | 1.5 mmol/l |
| Sodium chloride | 150 mmol/l |
| Sodium benzoate | 10 mmol/l |
| 3-[(3-Cholamidopropyl)dimethyl-ammonio]-1-propanesulfonate (CHAPS) | 2 mmol/l |
| 5-Chloro-2-methyl-4-isothiazolin-3-one/2-methyl-4-isothiazolin-3-one | 0.1% |
| Polyoxyethylene sorbitan monolaurate | 0.05% |
| Gelatin hydrolysate | 2% |

Performance of the determination:

300 µl of a washing solution consisting of isotonic sodium chloride solution and 0.05% polyoxyethylene sorbitan monolaurate are pipetted into the wells of a microtitre plate, whose inner surface is coated with a neopterin-specific antibody, and allowed to stand for 30 minutes. After the complete removal of this liquid, 50 µl of the reagent solution according to the invention are pipetted into each well, followed by in each case 50 µl of standards, controls and samples. After an incubation period of 30 minutes at room temperature, 50 µl of a buffered neopterin-horseradish peroxidase solution are added and incubation is continued for a further 60 minutes at room temperature. After washing twice with the abovementioned washing solution, 150 µl of a substrate solution of 3.8 mmol/l 2,2'-azino-di-(3-ethylbenzothiazoline-sulfonate) in 100 mmol/l citrate buffer, pH 4.3, are pipetted into the wells. After a further 30 minutes at room temperature, the substrate reaction is stopped with a 0.095% sodium azide solution and the extinction of the dye which has been formed is measured at 405 nm. The concentration of the samples is ascertained from the plotted calibration curve. The concentration of neopterin in the sample is inversely proportional to the measured signal.

Example 2

Comparison of the measured values in fresh and aged sera

| Neopterin [nmol/l] | Measured values of neopterin [nmol/l] | | | |
|---|---|---|---|---|
| | old serum | | fresh serum | |
| | with | without | with | without |
| | reagent solution according to Ex. 1 | | | |
| 5 | 5.3 | 5.2 | 4.7 | 11.2 |
| 10 | 11.5 | 10.6 | 10.1 | 17.1 |
| 15 | 16.1 | 16.2 | 16.0 | 21.9 |
| 20 | 21.1 | 21.5 | 20.1 | 26.4 |
| 25 | 24.5 | 25.3 | 24.8 | 29.1 |
| 35 | 35.4 | 36.3 | 37.9 | 41.8 |
| 45 | 46.9 | 45.9 | 43.3 | 50.8 |

The table shows the results of experiments with increasing concentrations of neopterin in fresh and aged sera. Known amounts of neopterin were added to the sera. Each sample was measured in duplicate. The neopterin determinations were preformed according to Example 1. For determinations made without the reagent solution according to Example 1, a second reagent solution was prepared having the same composition as in Example 1 but lacking the oxidizing agent. The samples were aged for about six months. It can be seen that the use of the reagent solution according to the invention from Example brings about an effective reduction of the apparently elevated neopterin concentrations in fresh serum.

Example 3

Determination of neopterin in relation to the added concentration of potassium hexacyanoferrate(III)

Performance of the determination takes place both according to Example 1 (sera Nos. 1 and 2) and analogously to Example 1, except that alkaline phosphatase is employed instead of horseradish peroxidase (sera Nos. 3 and 4).

Substrate: para-nitrophenyl phosphate
Stopping reagent: 0.1 mol/l sodium hydroxide solution
Wavelength: 405 nm The results of the neopterin determinations in fresh sera from healthy test subjects in relation to the added potassium hexacyanoferrate concentration in the reagent solution according to the invention are presented in the table below.

| Potassium hexacyano-ferrate (III) in the reagent [mmol/l] | Neopterin-HRP | | Neopterin-AP | |
|---|---|---|---|---|
| | Neopterin [nmol/l] Serum No. | | | |
| | 1 | 2 | 3 | 4 |
| 0 | 12.5 | 16.4 | 18.2 | 19.3 |
| 0.05 | 7.3 | 6.8 | 6.8 | 5.5 |
| 0.10 | 7.2 | 6.6 | 6.6 | 5.2 |
| 0.19 | 7.2 | 6.4 | 6.7 | 4.5 |
| 0.38 | 4.5 | 4.8 | 5.6 | 5.7 |
| 0.75 | 4.1 | 4.9 | 5.9 | 4.1 |
| 1.50 | 4.3 | 5.3 | 5.1 | 4.0 |
| 3.0 | 5.1 | 5.6 | 7.3 | 4.8 |
| 6.0 | 4.1 | 5.5 | 7.1 | 6.2 |
| 12.0 | 4.8 | 6.9 | 8.2 | 6.6 |
| 24.0 | 4.6 | 7.8 | 8.1 | 7.7 |
| 48.0 | 7.1 | 7.5 | 8.7 | 8.8 |

The table shows that, without the addition of Potassium hexacyanoferrate in the reagent solution, fresh sera exhibit neopterin concentrations which are apparently too high—at least by a factor of 2 to 3. For this to be the case, it is immaterial whether a neopterin-peroxidase conjugate or a neopterin-alkaline phosphatase conjugate is employed in the immunoassay. In the concentration range which is preferred according to the invention, neopterin concentrations are found which exhibit an excellent correlation with the established HPLC and RIA methods of determination. Analogous results are obtained if sodium hexacyanoferrate(III), iron(III) nitrate/EDTA, potassium persulfate, sodium perborate or sodium nitroprusside are employed instead of potassium hexacyanoferrate(III).

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A composition for treating body fluids in the immunological determination of neopterin using a specific antibody against neopterin, comprising:
   an antibody specific for neopterin or neopterin conjugated to a detectable label, and
   an effective amount of an oxidizing agent, wherein said oxidizing agent is potassium or sodium hexacyanoferrate(III), which reduces the amount of interference in said process by body fluid components.

2. A composition according to claim 1, wherein the oxidizing agent is potassium hexacyanoferrate(III).

3. A composition according to claim 1, wherein the concentration of said oxidizing agent is 0.05 to 100 mmol/l of potassium hexacyanoferrate(III).

4. A composition according to claim 1, wherein the concentration of said oxidizing agent is 0.5 to 50 mmol/l of potassium hexacyanoferrate(III).

5. A microtiter well containing within said well a solution, wherein the solution comprises a specific antibody against neopterin and an effective amount of an oxidizing agent, wherein said oxidizing agent is potassium or sodium hexacyanoferrate(III), which reduces the amount of interference by body fluid components in a process of immunological detection of neopterin by said antibody.

6. An immunoassay for the immunological detection of neopterin using a specific antibody against neopterin and a detection system, comprising:
   incubating the antibody and body fluids containing neopterin in the presence of an oxidizing agent, wherein said oxidizing agent is potassium or sodium hexacyanoferrate(III), which reduces the amount of interference by body fluid components in said process of immunological detection of neopterin by said antibody,
   detecting the amount of binding between the antibody and the neopterin, and
   correlating said amount of binding with the amount of neopterin in said body fluids.

7. The process according to claim 6, wherein the oxidizing agent is potassium hexacyanoferrate(III).

8. The process according to claim 6, wherein the concentration of said oxidizing agent is 0.05 to 100 mmol/l.

9. The process according to claim 6, wherein the concentration of said oxidizing agent is 0.5 to 50 mmol/l.

10. A competitive immunoassay for detecting neopterin in body fluids, comprising:
   incubating a sample of body fluid comprising neopterin with an antibody specific for neopterin and neopterin conjugated to a detectable label in the presence of an effective amount of oxidizing agent, wherein said oxidizing agent is potassium or sodium hexacyanoferrate(III), which reduces the amount of interferences by body fluid components;
   detecting the amount of binding between the antibody and the neopterin conjugated to a detectable label; and correlating said amount of binding with the amount of neopterin in said body fluid.

11. The immunoassay according to claim 10, wherein the oxidizing agent is potassium hexacyanoferrate(III).

12. The immunoassay according to claim 10, wherein the concentration of said oxidizing agent is 0.05 to 100 mmol/l.

13. The immunoassay according to claim 10, wherein the concentration of said oxidizing agent is 0.5 to 50 mmol/l.

14. A kit for detecting immunologically neopterin in body fluids, comprising:
- an effective amount of an oxidizing agent, wherein said oxidizing agent is potassium or sodium hexacyanoferrate(III) and which reduces the amount of interference by body fluid components;
- an antibody specific for neopterin; and
- neopterin conjugated to a detectable label.

15. A kit for detecting immunologically neopterin in body fluids, comprising:
- an effective amount of an oxidizing agent, wherein said oxidizing agent is potassium or sodium hexacyanoferrate(III), which reduces the amount of interference by body fluid components;
- an antibody specific for neopterin; or
- neopterin conjugated to a detectable label.

16. A composition according to claim 1, comprising said specific antibody against neopterin and said neopterin conjugated to a detectable label.

17. A competitive immunoassay according to claim 10, wherein the body fluids are fresh.

* * * * *